United States Patent

Kadowaki et al.

[11] 4,075,127
[45] Feb. 21, 1978

[54] CATALYST FOR PRODUCTION OF α,β-UNSATURATED CARBOXYLIC ACIDS

[75] Inventors: Koju Kadowaki; Kenji Takagi; Yoshiaki Tanaka, all of Ibaraki, Japan

[73] Assignee: Mitsubishi Petrochemical Company Limited, Japan

[21] Appl. No.: 713,593

[22] Filed: Aug. 11, 1976

[30] Foreign Application Priority Data

Aug. 18, 1975 Japan ............................. 50-99890

[51] Int. Cl.² .................... B01J 23/84; B01J 23/88
[52] U.S. Cl. ............................ 252/470; 260/530 N
[58] Field of Search .................. 252/470; 260/530 N

[56] References Cited

U.S. PATENT DOCUMENTS 3,574,729  4/1971  Gasson ........................ 252/470 X
3,956,377  5/1976  Dolhyj et al. ................ 252/470 X Primary Examiner—W. J. Shine
Attorney, Agent, or Firm—Robert E. Burns; Emmanuel J. Lobato; Bruce L. Adams

[57] ABSTRACT

An α,β-unsaturated aliphatic carboxylic acid can be prepared in a high yield by catalytic vapor phase oxidation of the corresponding α,β-unsaturated aldehyde in the presence of a catalyst represented by the following formula:

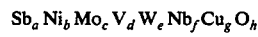

$$Sb_a Ni_b Mo_c V_d W_e Nb_f Cu_g O_h$$

wherein, $a = 100$, $b = 15 - 150$, $c = 10 - 500$, $d = 5 - 150$, $e = 0 - 100$, $f = 0 - 100$, $g = 0 - 50$ ($g \neq 0$ when $f = 0$), and $h \leq 2950$, respectively in atomic ratio. The catalyst has a long life time and gives a high yield even when it is contacted with a crude α,β-unsaturated aldehyde gas supplied by a catalytic vapor phase oxidation of the corresponding unsaturated hydrocarbon.

7 Claims, No Drawings

CATALYST FOR PRODUCTION OF α,β-UNSATURATED CARBOXYLIC ACIDS

BACKGROUND OF THE INVENTION

1. Field of the Invention

This invention relates to an improved catalyst for producing α,β-unsaturated aliphatic carboxylic acids via catalytic vapor-phase oxidation of the corresponding α,β-unsaturated aliphatic aldehydes.

2. Description of the Prior Art

It is known that α,β-unsaturated aliphatic carboxylic acids such as acrylic acid and methacrylic acid are prepared by a vapor-phase catalytic oxidation of α,β-unsaturated aliphatic aldehydes such as acrolein and methacrolein. Various catalysts to be used for the oxidation have been proposed.

For example, the catalysts for production of acrylic acid from acrolein are disclosed in, for example, Japanese Patent Publications Nos. 22,850/1965, 1,775/1966, 1,622/1967, 17,195/1967, 9,045/1968, 12,129/1969, 12,886/1969, 26,287/1969, 44/1972, 48,371/1972, 16,493/1973, and 19,296/1973, and Japanese Patent Laid-open Publications Nos. 2,011/1971, 8,360/1972, 18,823/1972, and 43,922/1974.

These proposed technics have improved or solved the problems to some extent. However, so far as the present inventors are aware, they are not always useful or satisfactory from the industrial viewpoint. These conventional catalysts have some defects in the various requirements for industrial catalysts such as a high reaction rate, a high yield, a long life time, satisfactory mechanical strength, reproducibility of production, and a simple condition of reaction.

Whether a catalyst satisfies these requirements or not depends mainly upon the inherent characteristics of the catalytic composition. In other words, the properties of a catalyst are more or less limited by the catalytic composition, although they may be varied according to the method of preparation, the method of activation, the use of carriers, and the like. Therefore, it is clear that selection of a proper catalytic composition itself is important so as to obtain the better results.

A catalyst consisting essentially of antimony, nickel, molybdenum and vanadium, which is similar to that of the present invention which is to be described in detail later, is disclosed in Japenese Patent Laid-open Publication No. 18,823/1972. A catalyst consisting essentially of antimony, nickel, molybdenum, vanadium and tungsten, which is also similar to that of the present invention, is disclosed in Japanese patent Laid-open Publication No. 43,922/1974. The latter catalyst is improved as to the yield of acrylic acid from acrolein, the life time of catalyst, reproducibility of production and the like, and is superior to the former catalyst. For example, the yield of acrylic acid with the former catalyst is 84.2% at 270° C, whereas the yield with the latter catalyst is 86.8% at 250° C.

SUMMARY OF THE INVENTION

An object of the present invention is to provide an efficient catalyst for producing α,β-unsaturated aliphatic carboxylic acids by subjecting the corresponding α,β-unsaturated aliphatic aldehydes to vapor-phase catalytic oxidation.

Another object of the invention is to provide an economical process for preparing α,β-unsaturated aliphatic carboxylic acids from the corresponding α,β-unsaturated aliphatic aldehydes via vapor-phase oxidation thereof in the presence of the catalyst.

Other objects of the invention will be obvious from the contents of the specification hereinafter disclosed.

These objects have been fulfilled by the present invention, whereby is provided a catalyst consisting essentially of antimony, nickel, molybdenum, vanadium, tungsten, niobium, copper and oxygen and represented by the following formula:

$$Sb_a Ni_b Mo_c V_d W_e Nb_f Cu_g O_h$$

wherein, Sb stands for the element of antimony, Ni for nickel, Mo for molybdenum, V for vanadium, W for tungsten, Nb for niobium, Cu for copper, and O for oxygen; the suffixes "$a - h$" represent the atomic ratio of each element, and when $a = 100$, then $b = 15 - 150$, $c = 10 - 500$, $d = 5 - 150$, $e = 0 - 100$, $f = 0 - 100$, and $g = 0 - 50$ ($g \neq 0$, when $f = 0$; and $h$ stands for the numbers of oxygen atoms when at least a portion of the above-mentioned elements exists in the state of oxides. The value of $h$ itself is determined by the valence requirements of the other elements present, and is determined according to the constitution of the other elements and the method of preparation of the catalyst. The value $h$ takes the maximum value as large as 2950 when all the values $a - g$ take their maximum values and these elements are in the form of the maximum-valent oxides, respectively.

When the values of $a - g$ are outside of the above-mentioned range, the features of the present invention can not be achieved. In general, the value is preferably in the following range;

$a = 100, b = 20 - 120, c = 15 - 400, d = 5 - 120,$
$e = 0 - 80, f = 0 - 80, g = 0 - 40$ ($g \neq 0$, when $f = 0$), and the maximum value of $h$ is 2,410.

The catalyst of the present invention is characterized in that the product is obtained in a high yield of acrylic acid, which will be as high as 91.2% at 270° C as shown in Example 1, as well as having an excellent stability, a long life-time and a wide range of allowance for reaction conditions. It is especially useful for the so-called two-stage continuous process which comprises the oxidation of an acrolein-containing gas as obtained by the catalytic oxidation of propylene.

DESCRIPTION OF THE INVENTION

1. Preparation of the Catalyst

The catalyst of the present invention is distinguished from the conventional catalysts in that the catalytic composition has the above-mentioned constitution and that nickel antimonate ($NiSb_2O_6$) may be formed from the antimony and nickel components in the most preferable composition. The formation of nickel antiomonate is preferable and advantageous for the properties of the resulting catalyst. By paying attention to this aspect, the conventional materials and methods for preparing this type of catalyst can be applied to the preparation of the present catalyst. The catalytic composition of the present invention can be incorporated with a coventional carrier component or supported on a porous molded carrier. For example, there can be employed carriers of silica, alumina, Celite (trade name), diatomaceous earth, alundum, carborundum and the like.

As to the materials for preparing the present catalyst, can be employed the corresponding metals, oxides thereof, hydrated oxides thereof, inorganic salts thereof, organic salts thereof and the like which can be converted to oxides by means of calcination. They include, for example, metallic antimony, antimony oxide, antimonate salts and the like as the antimony component; nickel nitrate, nickel chloride, and the like, as the nickel component; ammonium molybdate, molybdenum oxide, molybdic acid and the like, as the molybdenum component; ammonium vanadate, vanadium oxide, vanadyl oxalate, and the like, as the vanadium component; ammonium tungstate, tungsten oxide, tungnstic acid, and the like, as the tungsten component; niobium hydroxide, niobium oxalate, and the like, as the niobium component; and copper chloride, copper nitrate, and the like as the copper component.

In the following is illustrated an embodiment of preparing a catalyst of the present invention which comprises antimony, nickel, molybdenum, vanadium, niobium, copper and silica.

Antimony trioxide powder is added to an aqueous nickel nitrate solution. The resulting mixture is evaporated to dyness with stirring, followed by calcination at 300° - 1,000° C in the presence of air. Thus, $NiSb_2O_6$ is formed from the antimony and nickel components. According to their mixing ratio, antimony or nickel in excess may produce its oxide, but such oxide will not especially give an adverse effect to the resulting catalyst. The resulting powder is mixed with an aqueous solution of ammonium paramolybdate, ammonium metavanadate, niobium hydroxide, and cuprous chloride, followed by addition thereto of silica gel powder. The mixture is heated at 40° - 100° C to concentrate it to dryness.

The resulting mixture is then ground to power and, if desired, admixed with a lubricant such as graphite. The powder is tableted and then subjected to calcination.

The temperature of calcination is an important factor of the preparation of the catalyst. The calcination is desirably effected for about 1 - 10 hours at about 300° - 500° C and preferably at about 350° - 450° C, and can be carried out in an atmosphere of air, an exhaust gas from burners, oxygen diluted with an inert gas, or a weakly reducing gas and the like. The calcination temperature or atmosphere can also be varied in the course of calcination operation, and catalytic properties may be enhanced to some extent by employing suitable calcination conditions. When the catalytic composition of the present invention is to be carried on a molded porous carrier such as $\alpha$-alumina, alundum, or carborundum, the supported catalyst can be prepared, for example, by immersing the carrier in a solution containing the starting materials for the catalytic composition and heating the impregnated carrier to dryness, followed by calcination; or by drying the starting materials, calcining the resulting unmolded materials, grinding the calcined materials to powder, preparing a slurry thereof with water and coating the slurry on the carrier.

2. Use of the Catalyst

The method of using the catalyst of the present invention does not differ from the conventional methods for catalytic oxidation of acrolein or methacrolein.

The reaction is essentially carried out by passing a gas containing an $\alpha,\beta$-unsaturated aldehyde and molecular oxygen at a temperature in the range of about 230° - 380° C preferably 240° - 350° C, under a pressure of about 0.5 - 10 atmospheric pressure absolute preferably 1 - 5 atmospheric pressure absolute, and contacting the gas with the catalyst for about 0.5 - 20 seconds, preferably 1 - 10 seconds.

In this process, molecular oxygen is employed in an amount preferably about 0.2 - 5 times, the mole of the aldehyde being fed. In order to fully exhibit the catalytic properties, it is preferable to add steam as a diluent in a molar amount about 1 - 20 times of the aldehyde to the reaction gas.

The process for preparing an $\alpha,\beta$-unsaturated acid economically, by utilizing the properties of the present catalyst, involves a process for preparing an $\alpha,\beta$-unsaturated acid directly from the corresponding olefin via the so-called two-stage continuous process in which a catalyst for preparing an $\alpha,\beta$-unsaturated aldehyde through catalytic oxidation of an olefin and the catalyst of the present invention are respectively employed. For example, when acrylic acid is prepared from propylene, the reaction gas from the outlet of the first-stage reactor for producing acrolein can be introduced, without separation as it is, to the second-stage reactor packed with the catalyst of the present invention. If desired, oxygen or a diluent gas may additionally be introduced together with the reaction gas to the second-stage reactor. In this case, the catalysis by the present catalyst is not essentially affected by the presence of unreacted propylene or by-products from the first-stage reactor such as carbon monoxide, carbon dioxide, acetic acid, and acetaldehyde.

In the two-stage continuous process, the particulars of operation involved in the first stage, namely in the vapor-phase catalytic oxidation of $\alpha,\beta$-unsaturated olefins such as propylene, can be conventional ones.

In addition to the high yield obtainable, the catalyst in accordance with the present invention is further characterized by its long life time. Some catalysts for vapor phase oxidation of olefins or $\alpha,\beta$-unsaturated aldehydes maintain their initial activity for quite a short time in the run of oxidation process, but the catalyst in accordance with the present invention suffers little lowering of its activity in the run. Further, the catalyst in accordance with the present invention enjoys the significant increase in the selectivity during the course of oxidation.

Another advantage of the catalyst in accordance with the present invention is its high mechanical strength, which may be increased in the run of the oxidation process.

Accordingly, the present invention provides an oxidation catalyst suitable for use in commercial operation, whereby an economical production of acrylic acid is realized. Also, the present catalyst is advantageously employed as the catalyst for preparing methacrylic acid from methacrolein, in the same way as in the preparation of acrylic acid from acrolein.

The invention will be explained further in detail by examples, which are not limitative of the invention.

In the following examples, the conversion, yield and selectivity factor are indicated on a molar basis, unless otherwise specified.

EXAMPLE-1

Preparation of Catalyst

In 90 ml. of warm water 136 g of nickel nitrate is dissolved, and 159 g of antimony trioxide is slowly added thereto with stirring. The resulting slurry is heated to concentrate and subjected to drying at 90° C, followed by calcination at 800° C for 3 hours in a muffle furnace. The calcined product is ground to pass through a 60 mesh sieve (hereinafter referred to as powder A).

About 540 ml. of pure water is heated to about 80° C, and thereto are successively added with stirring 8.1g of ammonium paratungstate, 63.9 g of ammonium paramolybdate, 8.4 g of ammonium metavanadate, and 2.8 g of cuprous chloride. The resulting solution is slowly incorporated with the powder A, obtained above, with stirring to mix them completely. Then, 50 g of "Carplex #67" (amorphous silicon oxide hydrate, trade name supplied by Shionogi Co., Ltd., Japan) is added thereto, followed by mixing with stirring.

The resulting slurry is heated to 80° - 100° C to evaporate it to dryness with occasional stirring. The product is further dried at 90° C for 16 hours in a dryer and then ground to pass through a 24 mesh sieve.

The resulting powder is incorporated with 1.5% by weight of graphite, completely mixed, and molded into cylindrical tablets 5 mm. $\phi \times 4$ mm. by a tableting machine. The tablets are calcined at 400° C for 5 hours in a muffle furnace to prepare the catalyst.

The catalyst thus obtained has the following composition on a basis of atomic ratio.

Sb: Ni: Mo: V: W: Cu: Si = 100: 43: 35: 7: 3: 3: 80

It was observed that the main component of the powder A consisted of $NiSb_2O_6$ from the X-ray diffraction pattern of the powder A.

REACTION

Catalytic oxidation of acrolein was carried out with 50 ml of the catalyst which had been packed in a stainless-steel reaction tube having a niter bath jacket.

The gas consisting of 4% acrolein, 46% steam and 50% air was passed through the reaction tube at a space velocity of 870 (hour)$^{-1}$ on 0° C basis.

When the temperature of the niter bath was maintained at 270° C, the conversion of acrolein, the yield of acrylic acid, and the selectivity to acrylic acid were 97.9%, 91.2%, and 93.2%, respectively. The main by-products of the reaction were acetic acid, carbon dioxide, carbon monoxide, and acetaldehyde.

EXAMPLE-2

Preparation of Catalyst

The following catalyst was prepared in the same way as in Example-1, except for the atomic ratio of the catalyst, which was:

Sb: Ni: Mo: V: W: Cu: Si = 100: 43: 70: 14: 6: 6: 160

REACTION

Catalytic oxidation of acrolein was carried out at 270° C in the same way as in Example-1. The conversion of acrolein, the yield of acrylic acid, and the selectivity to acrylic acid were 98.8% 87.6%, and 88.7%, respectively.

EXAMPLE-3

Preparation of Catalyst

About 540 ml. of pure water is heated to about 80° C, and thereto are successively added with stirring 63.9 g of ammonium para-molybdate, 8.4 g of ammonium matavanadate, and 4.6 g of niobium hydroxide [NbO(OH)$_4$], to dissolve them. The resulting solution is slowly incorporated with 200 g of powder A (prepared as in Example-1) with stirring to mix them completely.

Then, 50g of "Carplex #67" is added thereto, followed by mixing with stirring. The resulting slurry is heated to 80° - 100° C with occasional stirring to evaporate it to dryness. The product is further dried at 90° C for 16 hours in a dryer and then ground to pass through 24 meshes sieve.

The resulting powder is incorporated with 1.5% by weight of graphite, completely mixed, and molded into cylindrical tablets 5 mm. $\phi \times 4$ mm. by a tableting machine. The tablets are calcined at 400° C for 5 hours in a muffle furnace to prepare the catalyst.

The catalyst thus obtained has the following composition on a basis of atomic ratio.

Sb: Ni: Mo: V: Nb: Si = 100: 43: 35: 7: 3: 80

REACTION

Catalytic oxidation of acrolein with this catalyst was carried out at 280° C in the same way as in Example-1. The conversion of acrolein, the yield of acrylic acid, and the selectively to acrylic acid were 94.4$, 86.2%, and 88.6%, respectively.

EXAMPLE-4

PREPARATION OF CATALYST

About 400 ml. of pure water is heated to about 80° C, and thereto are added 63.9 g of ammonium paramolybdate and 8.4 g of ammonium metavanadate to dissolve them. Separately, 18.4 g of oxalic acid is dissolved in 140 ml. of pure water and 9.2g of niobium hydroxide [NbO(OH)$_3$] is added thereto, followed by heating to about 80° C to dissolve it. The two solutions thus obtained are mixed, and then 200 g of powder A prepared as in Example-1 is slowly added thereto with stirring to mix them completely. Then 50 g of "Carplex #67" is mixed therewith with stirring. The resulting slurry is heated with stirring at 80° - 85° C for 2 hours, followed by concentration to dryness on a water bath. The product is further dryed at 90° C for 16 hours in a dryer and then ground to pass through 24 meshes sieve.

The resulting powder is incorporated with 1.5% by weight of graphite, completely mixed, and molded into tablets 5 mm $\phi \times 4$ mm by a tableting machine. The tablets are calcined at 400° C for 5 hours in a muffle furnace to prepare the catalyst.

The catalyst thus obtained has the following composition on a basis of atomic ratio.

Sb: Ni: Mo: V: Nb: Si = 100: 43: 35: 7: 6: 80

REACTION

Catalytic oxidation of acrolein with this catalyst was carried out at 230° C in the same way as in Example-1. The conversion of acrolein, the yield of acrylic acid, and the selectivity to acrylic acid were 94.3%, 86.5%, and 91.7%, respectively.

EXAMPLE-5

Preparation of Catalyst

About 540 ml. of pure water is heated to about 80° C, and thereto are successively added with stirring 63.9 g of ammonium paramolybdate, 8.4 g of ammonium metavanadate, 4.6 g of niobium hydroxide [NbO(OH)$_3$], and 2.8 g of cuprous chloride, to dissolve them. The resulting solution is slowly incorporated with 200 g of powder A prepared as in Example-1 with stirring to mix them completely. Then, 50 g of "Carplex #67" is added thereto and mixed with stirring.

The same procedure as in Example-1 was followed to obtain the catalytic composition having the following atomic ratio.

Sb: Ni: Mo: V: Nb: Cu: Si = 100: 43: 35: 7: 3: 3: 80

REACTION

Catalytic oxidation of acrolein with this catalyst was carried out at 270° C in the same way as in Example-1. The conversion of acrolein, the yield of acrylic acid, and the selectivity to acrylic acid were 97.7%, 85.3%, and 87.3%, respectively.

EXAMPLE 6

The two-stage continuous production of acrylic acid from propylene was carried out under pressure for 30 successive days, with two reaction tubes (stainless steel SUS-27) connected in series, each tube being 20 mm. in diameter and 600 mm. in length and equipped with a meter-bath jacket.

The first stage reaction tube was packed with 100 ml of a catalyst comprising substantially molybdenum oxide as the catalyst active for producing acrolein, and the second stage tube was packed with 60 ml of the catalyst which had been prepared in Example-2. The first stage tube was supplied with a gas mixture consisting of propylene, steam and air as shown in Table-1. The gas from the outlet of the first stage was directly introduced into the second stage tube.

The reaction conditions in each stage are shown in Table-1. The yields based on propylene and the yields of acrylic acid at the second stage based on acrolein fed to the second stage are shown in Table-2. The by-products obtained in each stage consisted substantially of carbon dioxide, carbon monoxide, acetic acid and acetaldehyde.

Table-1

| Material | First Stage | Second Stage |
|---|---|---|
| | propylene 5 %<br>steam 40 %<br>air 55 % | Product from the first stage reaction |
| Space velocity* | 450 (hour)$^{-1}$ | 750 (hour)$^{-1}$ |
| Reaction pressure (abs.) | 3 atm. | 3 atm. |

*based on gaseous volume at 0° C under 3 atm.

Table-2

| Days elapsed | | 1 | 7 | 20 | 30 |
|---|---|---|---|---|---|
| Reaction temperature | | | | | |
| first stage(° C) | | 330 | 330 | 330 | 330 |
| second stage(° C) | | 260 | 270 | 270 | 370 |
| Analysis | | | | | |
| at outlet of first stage | conversion of propylene(%) | 95.6 | — | — | 94.3 |
| | yield of acrolein (%) | 69.4 | — | — | 70.9 |
| | yield of acrylic acid(%) | 15.1 | — | — | 13.4 |
| at outlet of second stage | conversion of propylene(%) | 96.2 | 95.8 | 95.3 | 95.0 |
| | yield of acrolein (%) | 7.8 | 4.4 | 4.3 | 4.5 |
| | yield of acrylic acid(%) | 68.0 | 70.9 | 71.9 | 72.0 |

Table-2-continued

| Days elapsed | 1 | 7 | 20 | 30 |
|---|---|---|---|---|
| yield of acrylic acid(%) based on acrolein fed to second stage* | 76.2 | — | — | 82.7 |

*calculated by the following equation:
Yield of acrylic acid (%) based on acrolein $$\text{Yield} = \frac{\text{Increase in moles of acrylic acid in the second stage}}{\text{Moles of acrolein fed to the second stage}} \times 100$$

The "increase in moles of acrylic acid in the second stage" is equivalent to (yield of acrylic acid at outlet of second stage) — (yield of acrylic acid at outlet of first stage) and the "moles of acrolein fed to the second stage" is equivalent to (yield of acrolein at outlet of first stage).

By observing the change in reaction with the passage of time for one month, the catalyst of the present invention exhibited substantially stable properties under the given conditions on and after the 7th day of the reaction and was found to have a very long life time even under such conditions of use.

EXAMPLE 7

A two-stage continuous reaction was carried out by using the catalyst defined in Example-5 in the same way as in Example-6. The reaction was conducted under the conditions given in Table-1, except that the first stage catalyst of another lot was employed and the catalyst defined in Example-5 was used in the second stage reaction. The results are shown in Table-3. Under the given conditions, the yield of acrylic acid was in a somewhat increasing tendency on or after the 7th day of the reaction. The catalyst of the present invention was found to have a very long life time even under such conditions of use.

Table-3

| Days elapsed | | 1 | 7 | 20 | 30 |
|---|---|---|---|---|---|
| Reaction temperature | | | | | |
| first stage (° C) | | 330 | 330 | 330 | 330 |
| second stage (° C) | | 270 | 280 | 280 | 280 |
| Analysis | | | | | |
| at outlet of first stage | conversion of propylene(%) | 93.5 | — | — | 93.1 |
| | yield of acrolein(%) | 74.4 | — | — | 74.4 |
| | yield of acrylic acid(%) | 11.0 | — | — | 10.7 |
| at outlet of second stage | conversion of propylene(%) | 94.6 | 94.5 | 94.5 | 94.0 |
| | yield of acrolein(%) | 7.6 | 3.2 | 3.7 | 3.1 |
| | yield of acrylic acid(%) | 68.2 | 71.5 | 72.4 | 72.5 |
| | yield of acrylic acid(%) based on acrolein fed to second stage | 76.9 | — | — | 83.1 |

REFERENCE EXAMPLE

Preparation of Catalyst

To 700 ml of a conc. nitric acid, was added little by little 157 g of metallic antimony with stirring, to oxidize the antimony. After no nitrogen dioxide gas is generated, the mixture is incorporated with a solution of 157 g of nickel nitrate in 150 ml of pure water, followed by heating with stirring and evaporation to dryness. The resulting solid is ground to powder and calcined in air at 800° for 3 hours. This powder is added to a solution of 79.5 g ammonium paramolybdate and 10.5 g ammonium metavanadate dissolved with heating in 700 ml of pure water. The mixture is further incorporated with silica sol containing 54 g of $SiO_2$ and mixed. The resulting slurry is evaporated to dryness, ground to powder, and then calcined in air at 350° C for 1 hour.

The powder is admixed with 1% by weight of graphite powder, molded into tablets 4 mm.$\phi$ × 4 mm., and calcined in air at 380° C for 5 hours.

The elemental ratio of the resulting catalyst is calculated from the quantity of materials used to be in the following.

Sb: Ni; Mo: V (: Si) = 100: 42: 35: 7 (:70)

REACTION

The catalytic oxidation of acrolein was carried out with 50 ml of the catalyst thus prepared and packed in a stainless steel reaction tube of 20 mm. in inside diameter, by heating with niter bath. The material gas consisted of 4% acrolein, 46% steam and 50% air, and was passed at a space velocity of 870 (hour)$^{-1}$ based on 0° C.

At a bath temperature of 270° C, the conversion of acrolein, the yield of acrylic acid and the selectivity to acrylic acid were 96.6%, 83.1%, and 86.0%, respectively.

EXAMPLE 8

The catalyst having the following atomic ratio was prepared in the same way as in Example 5 except for the change in silica quantity.

Sb: Ni: Mo: V: Nb: Cu: Si = 100: 43: 35: 7: 3: 3: 20

The two-stage continuous reaction with this catalyst was carried out in the same way as in Example-6 and under the same conditions as in Table-1 except that the catalyst of other lot was used for the first stage reaction. The results are shown in Table-4. The efficiency of the present catalyst for the second stage reaction was increased after 30 days of the reaction by 5% in the yield of acrylic acid at the outlet of the second stage reactor. The yield of acrylic acid did not change for the period from 30 days to 80 days of the reaction. The catalyst of the present invention was found to maintain a very high yield and have a very long life time even under such conditions.

Table-4

| Days elapsed | | 1 | 30 | 80 |
|---|---|---|---|---|
| Reaction temperature | | | | |
| first stage (° C) | | 330 | 330 | 330 |
| second stage (° C) | | 270 | 270 | 270 |
| Analysis | | | | |
| at outlet of first stage | conversion of propylene (%) | 93.9 | 94.7 | 94.4 |
| | yield of acrolein(%) | 72.3 | 72.1 | 71.5 |
| | yield of acrylic acid(%) | 10.9 | 11.3 | 12.1 |
| at outlet of second stage | conversion of propylene(%) | 95.0 | 95.1 | 95.3 |
| | yield of acrolein(%) | 2.7 | 1.6 | 1.4 |
| | Yield of acrylic acid(%) | 71.8 | 76.8 | 76.8 |
| | yield of acrylic acid(%) based on fed acrolein | 84.2 | 90.8 | 90.5 |

EXAMPLE 9

Preparation of Catalyst

The catalyst having the following atomic ratio was prepared in the same way as in Example 5 except that silica was not incoporated.

Sb: Ni: Mo: V: Nb: Cu = 100 : 43 : 35 : 7 : 3 : 3

REACTION

The catalytic oxidation of acrolein was carried out at 250° C with this catalyst in the same way as in Example-1. The conversion of acrolein, the yield of acrylic acid, and the selectively to acrylic acid were 97.9%, 93.2% and 95.2%, respectively.

We claim:

1. A catalyst for production of an $\alpha,\beta$-unsaturated aliphatic carboxylic acid by the vapour phase oxidation of the corresponding $\alpha,\beta$-unsaturated aliphatic aldehyde, which consists essentially of an activated catalytic oxide complex of antimony, nickel, molybdenum, vanadium, tungsten, niobium, copper and oxygen and defined by the following formula:

$Sb_a Ni_b Mo_c V_d W_e Nb_f Cu_g O_h$ wherein, $a = 100$, $b = 15 - 150$, $c = 10 - 500$, $d = 5 - 150$, $e = 0 - 100$, $f = 0 - 100$, $g = 0 - 50$ wherein $g$ is not 0, when $f = 0$ and $h \leqq 2950$, which is a number determined by the valence requirements of the other elements present respectively, in atomic ratio.

2. A catalyst as set forth in claim 1, in which $a = 100$, $b = 20 - 120$, $c = 15 - 400$, $d = 5 - 120$, $e = 0 - 80$, $f = 0 - 80$, $g = 0 - 40$ wherein $g$ is not 0 when $f = 0$, and $h \leqq 2410$.

3. A catalyst as set forth in claim 1, in which the catalytic composition consists essentially of Sb, Ni, Mo, V, W, and Cu.

4. A catalyst as set forth in claim 1, in which the catalytic composition consists essentially of Sb, Ni, Mo, V, and Nb.

5. A catalyst as set forth in claim 1, in which the catalytic composition consists essentially of Sb, Ni, Mo, V, Nb and Cu.

6. A catalyst as set forth in claim 1, in which the catalytic composition consists essentially of Sb, Ni, Mo, V, W, Nb and Cu.

7. A catalyst as set forth in claim 1 in which, in said activated catalytic oxide complex, the nickel and antimony oxides occur as nickel antimonate.

* * * * *